(12) United States Patent
Murray

(10) Patent No.: US 6,905,567 B2
(45) Date of Patent: Jun. 14, 2005

(54) PROCESS FOR PRODUCTION OF COTTON SWABS

(75) Inventor: Liam Anthony Murray, Monroe, CT (US)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 243 days.

(21) Appl. No.: 10/410,677

(22) Filed: Apr. 10, 2003

(65) Prior Publication Data

US 2004/0200563 A1 Oct. 14, 2004

(51) Int. Cl.$^7$ .............................. B29O 31/00
(52) U.S. Cl. .................. 156/228; 19/145.3; 19/149; 156/293; 264/257; 264/271.1
(58) Field of Search .................. 19/145, 145.3, 19/149; 604/1; 264/250, 251, 257, 271.1, 299, 310; 156/228, 293; 425/233, 371, 372

(56) References Cited

U.S. PATENT DOCUMENTS

| | | | | |
|---|---|---|---|---|
| 3,154,818 A | * | 11/1964 | Nagle | 19/145.3 |
| 3,263,280 A | * | 8/1966 | Gustafson | 19/145.3 |
| 3,389,436 A | * | 6/1968 | Alden | 19/145.3 |
| 3,611,674 A | * | 10/1971 | Glickston | 53/72 |
| 3,698,040 A | * | 10/1972 | Mourkakos | 19/145.3 |

* cited by examiner

Primary Examiner—Jeff H. Aftergut
Assistant Examiner—John L. Goff
(74) Attorney, Agent, or Firm—Milton L. Honig

(57) ABSTRACT

A process and equipment for manufacture of a swab article is provided wherein a stick is placed onto a conveyor, adhesive is applied to one or both ends of the stick, a portion of cotton coil is attached to the adhesive bearing end, and a shaper bar or similar means forces the cotton to assume a teardrop profile by applying force parallel to the stick, wherein the shaper bar or similar means moves in a direction perpendicular to the stick at a different rate of speed than that of the stick. Differences in the rate of speed reduce tailing of cotton normally associated with drag.

4 Claims, 2 Drawing Sheets

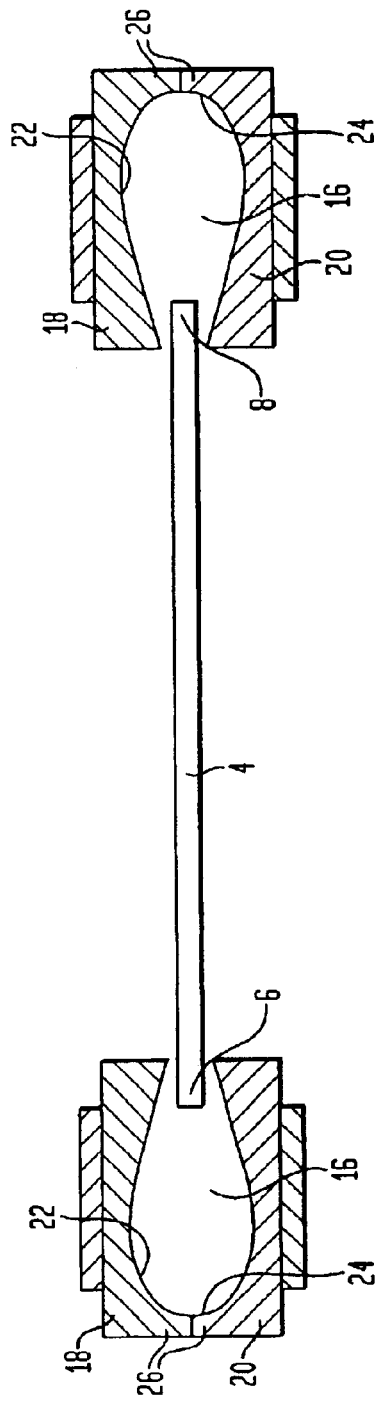
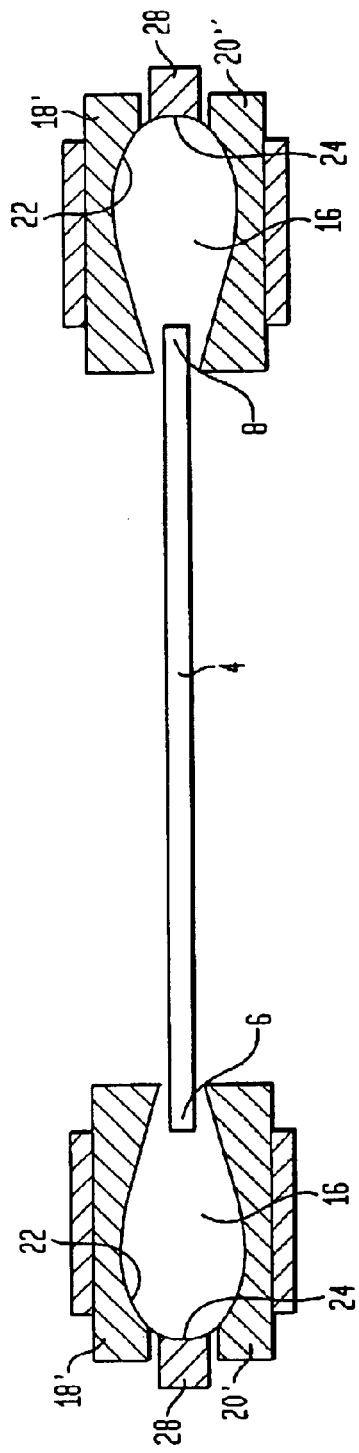

PROCESS FOR PRODUCTION OF COTTON SWABS

BACKGROUND OF THE INVENTION

1. Field of the Invention

The invention concerns a process and equipment for manufacture of cotton swabs at increased production speed.

2. The Related Art

Swabs are articles having an elongated stick formed of wood, plastic or tightly wound paper. One or both ends of the stick are covered with a small wad of absorbent cotton. These articles are most often used for personal hygiene such as cleaning ears, application of medicaments, application of cosmetics and even for hobbies such as painting.

Although manufacturing processes for swab articles are highly automated and well established, improvements are still sought which can increase production rates.

SUMMARY OF THE INVENTION

A process for manufacture of a swab article is provided which includes the steps of:

(i) placing a stick having first and second ends onto a conveyor;

(ii) applying adhesive to at least one of the first and second ends;

(iii) attaching a portion of cotton to the at least one end with the adhesive; and (iv) shaping the cotton by applying force through a shaping means against an end of the portion of cotton in a direction parallel to a length of the stick, the means moving in a direction perpendicular to the length of the stick.

DETAILED DESCRIPTION OF THE DRAWING

Advantages and features of the present invention may be more fully appreciated through the following detailed discussion, reference being made to the drawing in which:

FIG. 2 is a cross-sectional view of a swab article being processed through a shaper bar according to the present invention; and FIG. 3 is a cross sectional view similar to that of FIG. 2 except the shaper bar remains stationary while a traveling belt functions as the moving shaping means.

DETAILED DESCRIPTION OF THE INVENTION

Figure 1:
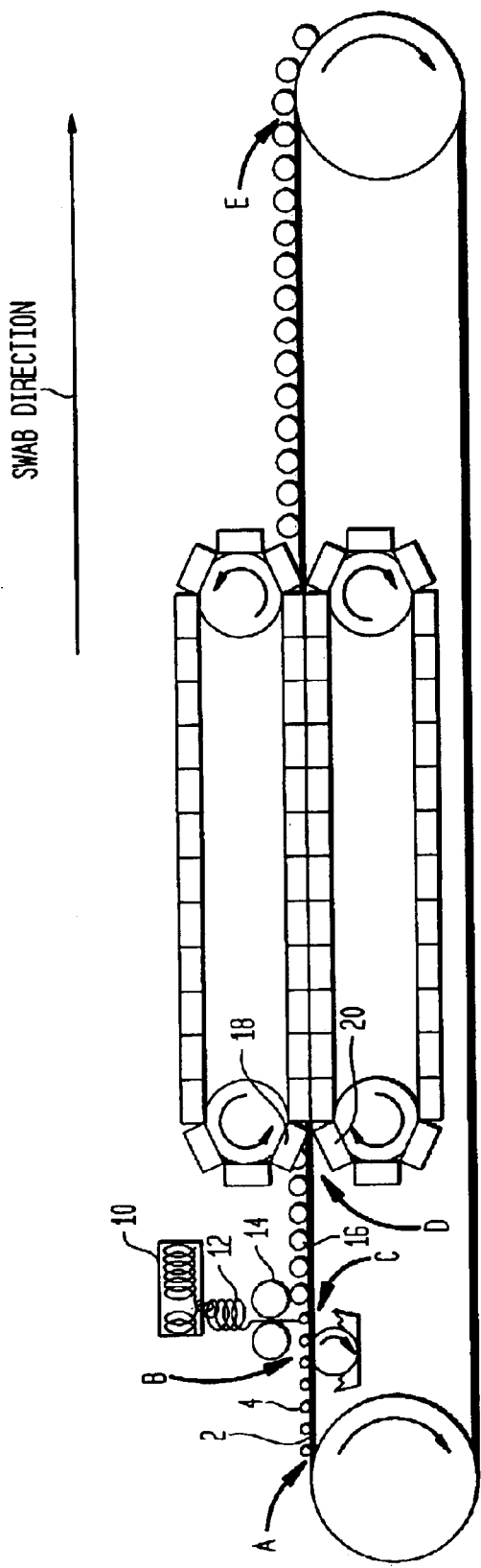
FIG. 1 is a schematic of the process according to the present invention.

FIG. 1 illustrates the process in operation. A conveyor 2 which may be a belt or chain is continuously operated in a loop. Individual swab sticks 4 are deposited onto the conveyor at station A. Clips attached to the conveyor hold individual sticks to prevent movement other than rotation. Downstream at station B adhesive is applied to both ends of each stick 6, 8.

A coil of cotton 12 is unwound from a bale 10 and fed through station C. There the coil is looped onto adhesively coated ends 6, 8 in a predetermined bud amount. Blocks 14 shear coil 12 to deliver the predetermined bud amount, all of which occurs at station C.

Further downstream, the sticks with their applied cotton bud enter station D. A section of shaper bar 18, 20 surrounds each cotton bud. The shaper bar 18, 20 may respectively be a single unitary bar or as illustrated in FIG. 1 be a series of sections each with a bud shaping profile 22. The shaper bar 18, 20 is motorized to travel at a different rate relative to the rate which the conveyor travels. Preferably, the rate of travel for the shaper bar will be faster than that of the conveyor. A particular advantage of the traveling shaper bar is that it maintains rotation of the swab article while reducing drag or friction. In turn, the travel of the shaper bar will reduce tailing associated with drag of cotton strands from the bud.

Still further downstream is a station E which identifies swab articles which have not been properly formed. These are rejected by being blown off the conveyor. The correctly manufactured swab articles are then sent to a packaging line for assembly and boxing.

FIG. 2 is a cross section which focuses upon station D. This Figure best illustrates shaper bar 18, 20 and the desired bud profile 22. Cotton tailing normally occurs near the apex 24 of the cotton bud 16. Movement of the shaper bars at a faster rate relative to and parallel to the conveyor minimizes tailing associated with friction.

FIG. 3 is a second embodiment of a means for reducing tailing. Instead of shaper bar portion 26 applying force in a direction parallel to the stick, a moving belt 28 could equally well serve to apply the parallel force against the apex of the cotton bud. In this embodiment, the shaper bar 18', 20' are static (non-moving) while the belt 18 undergoes movement. The belt may be in the form of a metal band or an elastomer.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The foregoing description and examples illustrate selected embodiments of the present invention. In light thereof variations and modifications will be suggested to one skilled in the art, all of which are within the spirit and purview of this invention.

What is claimed is:

1. A process for manufacturing a swab article comprising:

(i) placing a stick having first and second ends onto a conveyor;

(ii) applying adhesive to at least one of the first and second ends;

(iii) attaching a portion of cotton to the at least one end with the adhesive; and (iv) shaping the cotton by applying force through a shaping means against an end of the portion of cotton in a direction parallel to a length of the stick, the means traveling in a direction perpendicular to the length of the stick at a rate different from that of the conveyor.

2. The process according to claim 1 wherein the shaping means travels at a rate greater than that of the conveyor.

3. The process according to claim 1 wherein the shaping means travels at a rate slower than that of the conveyor.

4. The process according to claim 1 wherein the shaping means has a shape on a surface contacting the portion of cotton which is a teardrop shape.

* * * * *